(12) United States Patent
Gutt et al.

(10) Patent No.: US 9,750,592 B2
(45) Date of Patent: Sep. 5, 2017

(54) ARRANGEMENT FOR IMPLANTING AND METHOD FOR IMPLANTING

(76) Inventors: Carsten Nils Gutt, Lachen (DE); Hannes Goetz Kenngott, Heidelberg (DE)

( * ) Notice: Subject to any disclaimer, the term of this patent is extended or adjusted under 35 U.S.C. 154(b) by 177 days.

(21) Appl. No.: 13/123,272

(22) PCT Filed: Oct. 8, 2009

(86) PCT No.: PCT/EP2009/007233
§ 371 (c)(1),
(2), (4) Date: Jun. 20, 2011

(87) PCT Pub. No.: WO2010/040528
PCT Pub. Date: Apr. 15, 2010

(65) Prior Publication Data
US 2011/0245645 A1    Oct. 6, 2011

Related U.S. Application Data

(60) Provisional application No. 61/104,451, filed on Oct. 10, 2008.

(51) Int. Cl.
*A61N 1/05* (2006.01)
*A61F 2/00* (2006.01)
(Continued)

(52) U.S. Cl.
CPC .............. *A61F 2/0063* (2013.01); *A61N 1/05* (2013.01); *A61N 1/0507* (2013.01);
(Continued)

(58) Field of Classification Search
CPC .... A61N 1/0472; A61N 1/048; A61N 1/0488; A61N 1/0492; A61N 1/0507; A61N 1/0509; A61N 1/0517; A61N 1/056; A61N 1/0563; A61N 1/0565; A61N 1/057; A61N 1/0573; A61N 1/0587; A61N 1/059;
(Continued)

(56) References Cited

U.S. PATENT DOCUMENTS 4,089,704 A * 5/1978 Heiss et al. .............. 134/29
5,554,179 A   9/1996 Stroetmann et al.
(Continued)

FOREIGN PATENT DOCUMENTS

| JP | 2003526410 A | 9/2003 |
| JP | 2007527735 A | 10/2007 |
| WO | 2006/083617 | 8/2006 |

OTHER PUBLICATIONS

Office Action dated Sep. 17, 2013 from Japanese Patent Application No. 2011-530418 filed Dec. 22, 2011.
(Continued)

*Primary Examiner* — Allen Porter, Jr.
(74) *Attorney, Agent, or Firm* — Schmeiser, Olsen & Watts, LLP

(57) ABSTRACT

The invention relates to an arrangement for implanting in a human or animal body, comprising a carrier device which provides a receiving means and which is made from a synthetic mesh or fabric material, and an electronic element which is fixed to the carrier device in the region of the receiving means. Also provided is a method for implanting the arrangement in a human or animal body.

27 Claims, 4 Drawing Sheets

(51) Int. Cl.
*A61N 1/36* (2006.01)
*A61F 2/24* (2006.01)
*A61F 2/04* (2013.01)

(52) U.S. Cl.
CPC ....... *A61N 1/0517* (2013.01); *A61N 1/36007* (2013.01); *A61F 2/2481* (2013.01); *A61F 2002/044* (2013.01); *A61F 2250/0002* (2013.01)

(58) Field of Classification Search
CPC ............... A61N 1/0595; A61N 1/0597; A61N 2001/0578; A61N 2001/058
USPC ............................................ 607/40, 115, 116
See application file for complete search history.

(56) References Cited

U.S. PATENT DOCUMENTS

| | | | |
|---|---|---|---|
| 5,747,624 A * | 5/1998 | Rubinsztajn et al. ........... 528/21 |
| 6,416,474 B1 | 7/2002 | Penner et al. |
| 6,652,665 B1 * | 11/2003 | Sachdev et al. ................ 134/26 |
| 2001/0041821 A1 * | 11/2001 | Wilk ............................... 600/16 |
| 2002/0045926 A1 * | 4/2002 | Heil et al. ..................... 607/116 |
| 2002/0072744 A1 * | 6/2002 | Harrington et al. ............ 606/41 |
| 2002/0103424 A1 * | 8/2002 | Swoyer et al. ................ 600/350 |
| 2002/0177888 A1 * | 11/2002 | Williams et al. ............. 607/122 |
| 2002/0183628 A1 | 12/2002 | Reich et al. |
| 2003/0074041 A1 * | 4/2003 | Parry et al. ................... 607/130 |
| 2003/0083697 A1 * | 5/2003 | Baudino ............... A61N 1/0551 607/2 |
| 2003/0191502 A1 * | 10/2003 | Sharma ................ A61N 1/0587 607/9 |
| 2004/0260316 A1 | 12/2004 | Knudson |
| 2005/0020871 A1 | 1/2005 | Tozzi |
| 2005/0065396 A1 * | 3/2005 | Mortier et al. ................. 600/37 |
| 2005/0102010 A1 * | 5/2005 | Lau et al. ..................... 607/129 |
| 2006/0116736 A1 * | 6/2006 | DiLorenzo ..................... 607/40 |
| 2006/0224224 A1 * | 10/2006 | Muhlenberg et al. ........ 607/122 |
| 2007/0225545 A1 * | 9/2007 | Ferrari ........................... 600/17 |
| 2007/0239244 A1 * | 10/2007 | Morgan et al. ............... 607/119 |
| 2007/0239246 A1 * | 10/2007 | Camps et al. ................. 607/121 |
| 2008/0058887 A1 * | 3/2008 | Griffin et al. ................... 607/40 |
| 2009/0171376 A1 * | 7/2009 | Burton .................. A61M 25/02 606/151 |

OTHER PUBLICATIONS

Chinese Office Action issued Jun. 1, 2016; Application No. 200980149916.0; 23 pgs.

* cited by examiner

ARRANGEMENT FOR IMPLANTING AND METHOD FOR IMPLANTING

The invention relates to an arrangement for implanting in a human or animal body and also to a method for implanting the arrangement.

BACKGROUND OF THE INVENTION

Implants refer to materials and components which are introduced into a human or animal body in order to fulfill certain replacement or additional functions for a limited period of time or for life. Replacement functions include for example the assistance, control or partial or complete replacement of organ functions or also the assistance of healing processes, for example the immobilization of a bone fracture by means of osteosynthesis. In the case of osteosynthesis, implants which are usually made from metal are fixed to the bone, for example by means of nails or screws.

Artificial cardiac pacemakers for stimulating the heart are known from cardiac surgery. Cardiac pacemakers essentially comprise one or more electrodes which are fixed to the myocardium by sutures. For example, document EP 0 634 191 A2 discloses an implantable defibrillator comprising a flat electrode in the form of a mesh, a coil or a fabric made from electrically conductive material or comprising an intracardial electrode in the form of a coil made from electrically conductive material, wherein the electrode is completely embedded in a biocompatible, hydrophilic, electrolytically conductive polymer or is coated with such a polymer. The defibrillator is fixed in the subcutaneous tissue by customary fixing means such as barbs and pins.

Furthermore, so-called gastric pacemakers are known from obesity therapy. Gastric pacemakers generally consist of two electrodes which are introduced into the gastric wall by means of a needle. A wire connects the electrodes to a pacemaker, which is placed in a subcutaneous pocket below the left costal arch and can be programmed from outside. In the region of the gastroesophageal transition, a suitable location on the gastric wall is selected at which the electrodes are intended to come to rest intramurally, that is to say in the organ wall. The entry and exit point of the needle are usually approximately 2.5 cm apart, with the entry and exit points being marked by an electrocauter. The electrodes are then introduced under gastroscopic monitoring, in order to prevent any perforation of the gastric wall. The probe is secured proximally by two sutures and distally by means of a clip or a barb. The lead is then passed outside the body and connected there to the pacemaker. Also known are implantable gastric bands which are placed around the fundus of the stomach in a laparoscopic operation. The gastric band may be made for example from silicone. By constricting the diameter of the stomach, a long-term significant reduction in weight is said to be achieved since then a smaller amount of food is sufficient to reduce or eliminate the feeling of hunger of the patient.

From reflux surgery, various devices are known which can be implanted in the body in order to reduce reflux. The term "reflux" generally refers in medicine to a pathological return flow from one hollow organ to another. Examples of refluxes include: gastroesophageal reflux—from the stomach to the esophagus, which may lead to heartburn or to reflux esophagitis; hepatojugular reflux—from the heart to the external jugular vein in the event of pressure on the liver; and vesicorenal reflux—from the urinary bladder via the ureter to the kidney. Such a device which can be implanted in the body consists of a mesh which is placed around the esophagus. Clinical and experimental studies, particularly in hernia surgery and in reflux surgery, have shown that such meshes are well accepted by the body and do not exhibit any tendency to migrate through organs.

One common feature of all known implants is the need to fix the implant securely to an organ or to an organ part. The term "organ" generally refers in medicine to parts of the body which are composed of cells and tissue and which form a unit having specific functions, for example the esophagus, the stomach, the intestine, the esophageal sphincter, the bladder muscle, other sphincters. The fixing operation often leads to traumatic damage to the organ. For example, when fixing the electrodes of a gastric pacemaker, such damage may lead to a weakness of the gastric wall, which might result in a rupture of the gastric wall. However, if the electrodes are fixed in such a way that damage to the gastric wall is largely avoided, the probability of the electrodes slipping in the gastric wall or even slipping out of the gastric wall would be significantly increased as a result.

Known implantable devices have the disadvantage that fixing to an organ or to an organ part causes traumatic damage to the organ wall, wherein the devices often dislocate despite being fixed.

SUMMARY OF THE INVENTION

The object of the invention is to provide an improved arrangement for implanting in a human or animal body and a method for implanting the arrangement, which avoid the abovementioned disadvantages and allow a fixing of electronic elements in the human or animal body in such a way that is gentle on the organ and at the same time secure.

According to the invention, this object is achieved by an arrangement for implanting in a human or animal body and by a method for implanting the arrangement. Also provided are a use of the arrangement for implanting and a use of the method for implanting. Advantageous embodiments of the invention form the subject matter of dependent claims.

The invention encompasses the concept of an arrangement for implanting in a human or animal body, comprising a carrier device which provides a receiving means and which is made from a synthetic mesh or fabric material, and an electronic element which is fixed to the carrier device in the region of the receiving means.

The invention also encompasses the concept of a method for implanting an arrangement in a human or animal body, in which an arrangement comprising a carrier device which provides a receiving means and which is made from a synthetic mesh or fabric material, and an electronic element which is fixed to the carrier device in the region of the receiving means, is provided and then implanted by placing the carrier device on a tissue section in the interior of the body.

Also provided is the use of the arrangement for implanting in a therapy selected from the following group of therapies: obesity therapy, reflux therapy, continence therapy, achalasia therapy, myopathy therapy, dystrophy therapy, epilepsy therapy, neurosurgical therapy, constipation therapy and neuralgia therapy.

Also provided is the use of the method for implanting the arrangement in a therapy selected from the following group of therapies: obesity therapy, reflux therapy, continence therapy, achalasia therapy, myopathy therapy, dystrophy therapy, epilepsy therapy, neurosurgical therapy, constipation therapy and neuralgia therapy.

According to the invention, an electronic element is fixed to a carrier device made from a synthetic mesh or fabric material. The electronic element is fixed to the carrier device for example by means of hooks or staples. As an alternative or in addition, the electronic element may also be woven into the mesh or fabric material. In one embodiment, a holder, that is to say a device for fixing a replaceable element, may be fixed to the carrier device. The electronic element preferably has a base associated with a receiving means of the holder. It is thus possible to fix the electronic element releasably and replaceably on the carrier device. In one embodiment, the electronic element and the carrier device are formed as an integrated unit. By way of example, the carrier device may be adhesively bonded to the electronic element.

In order to arrange the electronic element on an organ or an organ part or a tissue/tissue section, the carrier device is fixed to the organ or the organ part for example by means of staples, sutures or pins. As an alternative or in addition, however, the carrier device may also be adhesively bonded to the organ by means of an adhesive, in particular a fibrin adhesive. By way of example, it may also be provided that the electronic element has at least a thorn and/or at least a pin or is formed in a thorn shape, preferably in a pin-shaped. By way of example, it may also be provided that the pins or the thorns have each a different length. Preferably, the electronic element and the thorn are formed in an integrated manner. The thorn or the thorn-shaped or the pin-shaped electronic element is inserted into the organ or the organ part and thus ensures fixing. In one embodiment, the mesh or fabric material has a three-dimensional surface shape, for example a pyramid shape or a cone shape.

Preferably, the synthetic mesh or fabric material is made from a scar-forming material or has a coating made from such a material. A scar-forming material, upon contact with human or animal tissue, triggers an inflammation reaction in the organ tissue, as a result of which a scar tissue is formed. The scar tissue partially or even completely surrounds the carrier device and thus fixes the carrier device with the electronic element securely to the organ tissue.

Unlike in the prior art, in which electronic elements are fixed directly to the organ, in the invention the electronic element is thus fixed to a carrier device and the latter is then fixed to the organ.

One preferred embodiment of the invention provides that the electronic element has a feed electrode which is configured to emit electrical pulses. In particular, the feed electrode is formed with a rod shape, a ring shape or a needle shape. By way of example, it may be provided that the electronic element has several feed electrodes.

In another preferred embodiment of the invention, the electronic element has a probe electrode which is configured to detect measurement signals. In particular, it is possible to detect the measurement signals for a physiological parameter. A physiological parameter may be for example an excitation profile, a temperature, a resistance, a movement, a position, a laboratory parameter, in particular a pH value, or a vital parameter, in particular an electrocardiogram (ECG). Preferably, the probe electrode is formed with a ring shape, a rod shape or a needle shape. In one preferred embodiment, the electronic element has a probe electrode and a feed electrode, and in particular it may be provided that the probe electrode and the feed electrode is designed as an integrated electronic component, for example as an electrode which is configured both as a feed electrode and as a probe electrode.

In a purposeful further development of the invention, it may be provided that the electronic element has a pacemaker which is configured to emit pacemaker pulses. In particular, in addition to the pacemaker, a probe electrode and/or a feed electrode may also be fixed to the carrier device. An integrated electronic component may also be provided which comprises both the pacemaker and the probe electrode and/or the feed electrode. In one preferred embodiment, the feed electrode is configured to emit electrical pulses in a manner corresponding to the pacemaker pulses. In a further example of embodiment, the pacemaker is configured to evaluate the measurement signals of the probe electrode and to emit pacemaker pulses corresponding to the evaluation. Preferably, the pacemaker is configured to actuate probe electrodes and/or feed electrodes individually in each case. By way of example, the feed electrodes are fixed to a first carrier device, the probe electrodes are fixed to a second carrier device and the pacemaker is fixed to a third carrier device.

In a further preferred embodiment of the invention, the electronic element has a signal terminal which is configured to couple an electrical signal link to the electronic element. By way of example, the signal terminal is configured for a wired signal link, for example a cable terminal. As an alternative or in addition, it may be provided that the signal terminal is configured for a wireless signal link, for example for an inductive and/or capacitive signal link. By means of the wired and/or wireless signal link, control signals for example are transmitted to the electronic element and/or from the electronic element to further electronic elements, for example a pacemaker. In order to transmit the signals, it is not absolutely necessary for the electronic elements to be fixed to a common carrier device, but instead the electronic elements may be fixed to a plurality of carrier devices arranged at a distance from one another. It is also possible that a probe electrode for example detects measurement signals and transmits these measurement signals to a pacemaker. The pacemaker evaluates the measurement signals and then transmits pacemaker pulses to a feed electrode, which emits corresponding electrical pulses.

In a purposeful further development of the invention, it may be provided that the electronic element has a supply terminal which is configured to receive an electrical power supply for the electronic element. Preferably, the electrical power supply comprises a voltage supply. In one preferred further development, it may be provided that a power supply device is fixed to the carrier device. By way of example, the power supply device comprises at least one battery and/or at least one rechargeable battery. In one further development, it may be provided that the electronic element is configured for a wireless power supply, in particular for an inductive power supply.

In one example of embodiment of the invention, the electronic element has a data terminal which is configured to couple an electronic data link to the electronic element. In particular, the data terminal is configured for a wired data link. As an alternative or in addition, the data terminal is configured for a wireless data link, in particular WLAN, Bluetooth, IrDA. By means of the electronic data link, data, in particular measurement data and/or control data, are transmitted from the electronic element to further electronic elements, which are located inside or outside the body, and/or to the electronic element. Preferably, the measurement data are formed according to measurement signals from a probe electrode. By means of the electronic data link, the measurement data are transmitted for example to a pacemaker. The pacemaker evaluates the measurement data. However, it may also be provided that a further electronic element, for example a processor device, in particular a computer, evaluates the measurement data and forms and provides control data corresponding to the evaluation. By way of example, the processor device may be fixed to the carrier device. It is thus possible for the pacemaker to emit pacemaker pulses in a manner corresponding to the control data, preferably to a feed electrode. Preferably, the measurement data and/or the control data are stored in a memory device, it being possible for the memory device to be formed in such a way that it is integrated in the pacemaker. The measurement data and/or the control data can thus also be retrieved at later points in time. In a further preferred embodiment, the data terminal is formed in an integrated manner in the electronic element. Preferably, the electronic element has further terminals, preferably integrated in the electronic element, such as signal terminals or supply terminals for example.

In one preferred further development of the invention, the synthetic mesh or fabric material is formed according to at least one material configuration selected from the following group of material configurations: plastic mesh, plastic-coated mesh, metal mesh, synthetic fibers, material of plant origin, metal material, organic material, inorganic material, at least partially resorbable material and electrically conductive material. Preferably, the mesh is made from a flexible material. This makes it possible for the carrier device to be adapted easily to the shape of the organ or tissue. By way of example, it may be provided that the artificial mesh or fabric material is formed from a metal mesh which is partially or completely coated with plastic. In a purposeful embodiment, the mesh or fabric material comprises an adhesive agent, for example a glue. Preferably, the mesh or fabric material is at least partially formed of the adhesive agent. The adhesive agent may comprise for example a fibrin adhesive. Furthermore, it may be provided in one embodiment that the mesh or fabric material is at least partially formed from a so-called intelligent textile. Intelligent textiles usually refer to a combination of a textile and an additive integrated in the textile. The additive may comprise for example a chemical substance, in particular a medicinal active ingredient. Furthermore, the additive preferably comprises electronic components, in particular conductor tracks, which provide for example an electrical connection between the electronic element and the organ or the tissue. By way of example, the conductor tracks are woven into the mesh or fabric material. In one advantageous embodiment, the conductor tracks provide an electrical signal link and/or an electronic data link. The electronic element and the synthetic mesh or fabric material thus form an integrated unit.

In a purposeful further development of the invention, an opening is formed in the region of the receiving means. The opening is preferably ring-shaped. The opening is substantially adapted to the shape of an organ or an organ part. By way of example, in the case of a ring-shaped opening, the carrier device may be arranged around the esophagus. In one further development, the synthetic mesh or fabric material may have a three-dimensional surface shape, with the opening being formed in one region of the three-dimensional surface shape. By way of example, the opening may be formed on a base surface or on a top surface of a truncated cone.

In one example of embodiment of the invention, it may be provided that the electronic element is arranged adjacent to the opening. Preferably, a plurality of sub-elements are distributed around the opening. By way of example, the plurality of sub-elements comprise feed electrodes and/or probe electrodes. An arrangement which surrounds an organ section is thus possible.

In another preferred embodiment of the invention, the carrier device and the electronic element fixed to the carrier device are configured to be implanted on or in an organ or an organ part selected from the following group of organs/organ parts: esophagus, stomach, reflux muscle, heart, bladder, sphincter, rectum, cardia, fundus, corpus.

Further advantageous embodiments of the method for implanting an arrangement in a human or animal body will be explained in more detail below.

One preferred further development of the invention provides that the step of provisional fixing comprises a step of adhesively bonding the carrier device to the tissue section. By way of example, the carrier device may be adhesively bonded to the tissue section by means of a fibrin adhesive. As a result, it is possible to be gentle on particularly sensitive tissue, since there is no need to fix the carrier device to the tissue section by means of sutures or staples. Preferably, the fibrin adhesive comprises a physiological two-component adhesive, preferably of biological origin. In one preferred embodiment, the two-component adhesive comprises fibrinogen and factor VIII as the first component and thrombin as the second component. When the first and the second component are mixed, the thrombin cleaves fibrinogen into fibrin and activates factor VIII to form factor VIIIa. Factor VIIIa leads to a crosslinking of the fibrin, which results in a stable, tear-resistant but at the same time also elastic fibrin mesh which at least partially surrounds the carrier device. The fibrin mesh is dissolved over time by enzymes within the body, for example the enzyme plasmin. This process is known as fibrinolysis. For this reason, the fibrin mesh fixes the carrier device to the tissue section only provisionally. Preferably, the first component additionally comprises aprotinin. Aprotinin delays fibrinolysis by binding to the enzyme plasmin. However, because this is a reversible binding process, the plasmin does not become unusable but rather is merely hindered in its function. As a result, the lyzing effect is slowed. The carrier device can therefore be provisionally fixed to the tissue section for a longer period of time. By way of example, the second component comprises calcium chloride. Calcium chloride assists the natural coagulation of blood and thus a wound healing process. In a purposeful embodiment, the two components are applied, in particular by spraying, preferably by means of a double spray, to the tissue section successively, that is to say one after the other, i.e. firstly the first component and then the second component, or simultaneously, that is to say both components at the same time. As an alternative or in addition, the carrier device may also be adhesively bonded to the tissue section by means of cyanoacrylate or other tissue adhesives.

In an advantageous further development of the invention, the step of provisional fixing comprises a step of mechanically attaching the carrier device to the tissue section using mechanical fixing means. These are for example hooks, barbs, staples, clips, sutures, thorns, pins or stitches. Preferably, the fixing means are formed from a bioresorbable material or are coated with such a material. The carrier device may thus for example be stitched onto the tissue section, for example by means of stitches made from a bioresorbable material which are then absorbed by the body over time. In particular, it may also be provided to stitch the carrier device onto the tissue section and additionally fix it to the tissue section by means of hooks, barbs, staples and/or clips. In a purposeful embodiment, it may be provided that the carrier device is provisionally fixed to the tissue section by introducing one or more thorns into the tissue section. Preferably, it may be provided that the thorn(s) are formed on the electronic element, with the electronic element then being introduced into the tissue section for provisional fixing purposes.

In another preferred embodiment of the invention, a step is also provided for permanently fixing the arrangement to the tissue section as a result of the fact that scar formation takes place on the tissue section around the carrier device. The scar formation is the result of an inflammation reaction of the tissue on contact with the carrier device. The scar or the scar tissue partially or completely surrounds the carrier device and thus permanently fixes the arrangement to the tissue section. Preferably, the carrier device comprises a scar-forming material. This helps to particularly promote scar formation. In one preferred embodiment of the invention, the carrier device is adhesively bonded to the tissue section by means of a fibrin adhesive. By means of the fibrin adhesive, a fibrin mesh is formed which provisionally fixes the carrier device to the tissue section. The fibrin mesh is dissolved or lyzed by the body over time but, since the scar formation takes place at the same time, the carrier device remains permanently fixed to the tissue section. A permanently fixing to the tissue section is thus achieved without the tissue being traumatically damaged by mechanical fixing means.

A purposeful further development of the invention moreover provides a step for feeding stimulation pulses to the tissue section via the electronic element having a feed electrode. When for example stimulation pulses are fed to the stomach, the emptying of the stomach can thus be accelerated. If stimulation pulses are fed to the esophagus, a closing pressure of the esophageal sphincter is increased, as a result of which acid reflux is reduced. In particular, the vagus nerves running along the esophagus can also be stimulated, in particular can be stimulated in an isolated manner. A direct placement and fixing of feed electrodes on the esophagus is difficult since this is a tube made from muscle. However, since it is provided to fix the feed electrodes to the carrier device and then to fix the latter to the organ, the stimulation of the esophagus is thus now possible, which was not possible to date in the prior art. In particular, several regions of the esophagus can be stimulated in a targeted manner.

In one embodiment of the invention, a step may also be provided for detecting measurement signals for the tissue section via the electronic element having a probe electrode. Preferably, physiological parameters of the organ or of the organ part are detected. In particular, the measurement signals may be evaluated, for example by means of a pacemaker. One preferred embodiment provides that stimulation pulses corresponding to the evaluation are fed to the organ or to the organ part by means of a feed electrode. It is thus possible to firstly detect a state of the tissue section and to then stimulate the tissue section accordingly.

In another embodiment of the invention, a step may also be provided for emitting pacemaker pulses to the feed electrode and/or to the probe electrode via the electronic element having a pacemaker. The pacemaker pulses control for example the feed electrode in such a way that these stimulation pulses are fed to the tissue section with a predefined frequency and/or a predefined intensity. Preferably, the pacemaker pulses control the probe electrode in such a way that the probe electrode detects measurement signals for the tissue section in a predefined time window. By way of example, firstly measurement signals are detected, and then the tissue section and thus the organ is stimulated. Preferably, the pacemaker is configured to actuate the feed electrode and the probe electrode individually.

It is thus possible for example to fix a plurality of feed electrodes and/or probe electrodes to one carrier device and to actuate said electrodes in each case individually by means of the pacemaker pulses. By way of example, the probe electrodes may be fixed to the stomach and the feed electrodes may be fixed to the esophageal sphincters. Then, when the measurement signals indicate that the stomach is filled up to a certain part and thus the risk of acid reflux is particularly high, the esophageal sphincters are stimulated by means of the feed electrodes so that they do not open uncontrollably.

In one further development of the invention, an electrical signal link is coupled to the electronic element. By way of example, the electrical signal link may be coupled to the electronic element by means of a cable. Preferably, the electrical signal link is coupled to the electronic element in a wireless manner, for example in an inductive and/or capacitive manner. In one preferred embodiment, control signals are transmitted to and/or from the element by means of the electrical signal link.

In a purposeful embodiment of the invention, the electronic element is supplied with electrical power, preferably with a voltage. By way of example, the electrical power is provided by a power supply device. The power supply device comprises for example a battery and/or a rechargeable battery. In particular, the power supply device is fixed to the carrier device. However, it may also be provided to implant the power supply device in the body at a distance from the arrangement. By way of example, the power supply device may be fixed to a carrier device and then may be fixed intracorporally, that is to say in the interior of the body, for example in the region of the abdominal wall, preferably in a costal arch region. In particular, the power supply device may also be fixed extracorporally, that is to say outside the body. In another embodiment, it may be provided that the electronic element is supplied with electrical power in a wireless manner, for example by means of induction.

In another further development of the invention, an electronic data link is coupled to the electronic element. By way of example, the electronic data link is coupled to the electronic element by means of a cable. However, it may also be provided to couple the electronic data link to the electronic element in a wireless manner. By means of the electronic data link, in particular measurement data and/or control data can be transmitted to/from the electronic element. By way of example, data, preferably measurement data, are transmitted to a pacemaker.

In a further purposeful embodiment, it may be provided to introduce the arrangement into the human or animal body by means of a laparoscopic operating method. In laparoscopic operating methods (laparoscopy), the abdominal cavities and the organs located therein are made visible by means of special rod-shaped lens optics (rigid endoscopes) via small openings made in the abdominal wall by the surgeon. Through a cut in the skin measuring preferably approximately 0.3 cm to 2 cm in length, a so-called trocar is inserted into the abdominal wall, though which it is then possible to see into the abdominal space using a special endoscope (laparoscope) which is connected to a video camera and a light source. In the case of diagnostic laparoscopy, after the abdominal space has been inspected, the instrument is removed again and the wound in the abdominal wall is closed by suturing. In the case of an operative intervention, additional instruments are introduced through further cuts in the skin which likewise measure preferably approximately 0.3 cm to 2 cm, by means of which additional instruments the operation can be carried out.

During a laparoscopic procedure, firstly the abdominal space is filled with gas until a so-called pneumoperitoneum is created. This may be carried out using various methods. One of these consists in using a surgical scalpel to make a small cut in the skin in the region of the navel, since at that point in particular the abdominal wall is at its thinnest and the distance from the abdominal organs is greatest. Then, using a special insufflation cannula (Veress cannula or Veress needle), the abdominal wall is passed though only so far until finally the blunt tip thereof, at which the insufflation opening is located, is located freely in the abdominal space. The tube of an insufflation pump can then be connected to the Veress cannula and the abdominal space can be "pumped up" with carbon dioxide ($CO_2$) until a kind of "working and investigation space" is created. This space (intra-abdominal space) then has to be made accessible endoscopically. For this purpose, depending on the type of planned intervention, as described above, further small incisions are made in the abdominal wall, via which trocar sleeves which close in a gas-tight manner are inserted and securely anchored. By means of these "keyhole openings", which are also referred to as "trocar access holes", the endoscope and the special surgical instruments can be manually controlled by the operator or the assistant.

In an alternative, less widely known laparoscopic method, gasless laparoscopy, the abdominal wall is mechanically raised by means of a lift system.

In another preferred embodiment of the invention, the arrangement is implanted on a tissue section of an organ or an organ part selected from the following group of organs/organ parts: esophagus, stomach, reflux muscle, heart, bladder, sphincter, cardia, fundus, corpus, vagus nerve, brain, muscles, nerves, pelvic floor and rectum.

DESCRIPTION OF EXAMPLES OF EMBODIMENTS OF THE INVENTION

The invention will be explained in more detail below on the basis of examples of embodiments and with reference to figures of a drawing, in which.

Figure 1:
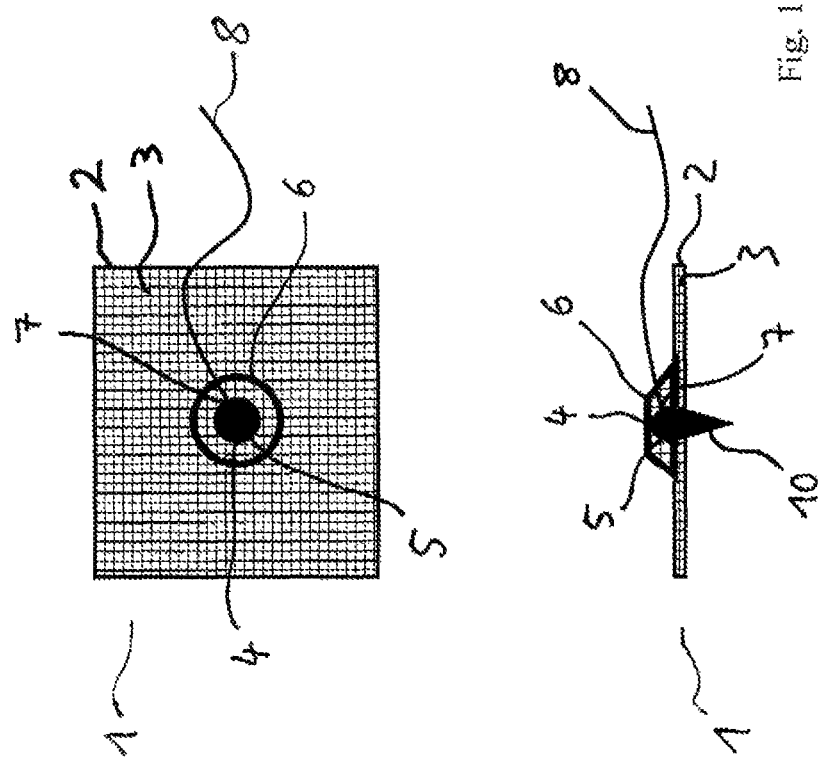
FIG. 1 shows an arrangement for implanting in a human or animal body, comprising a plastic mesh and a feed electrode.
Figure 2:
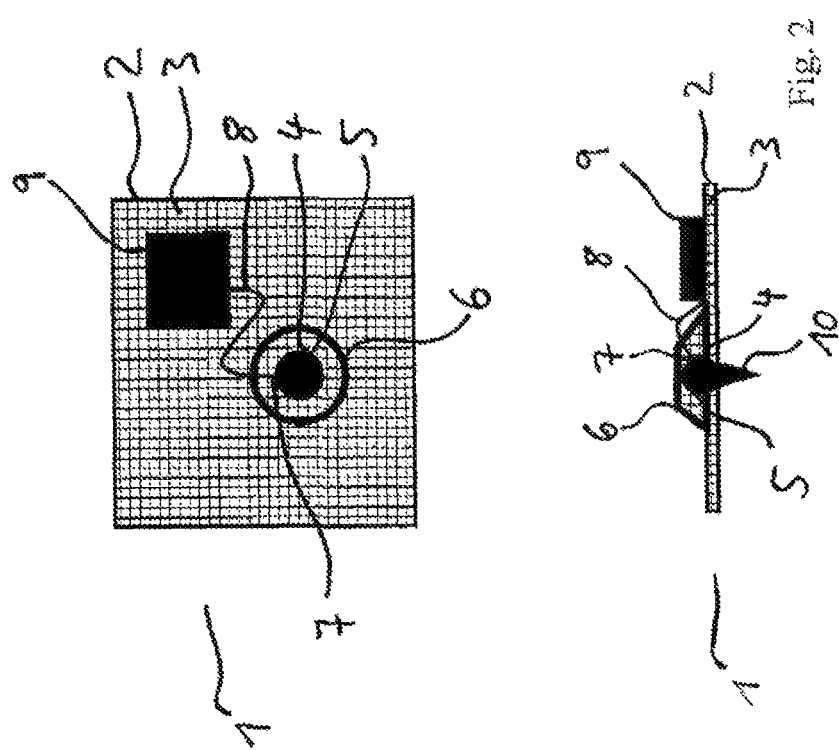
FIG. 2 shows the arrangement shown in FIG. 1 with a pacemaker.

FIGS. 1 and 2 show an arrangement 1 for implanting in a human or animal body with a carrier device 2. The carrier device 2 is formed from a plastic mesh 3, to which a holder 6 is fixed. The holder 6 releasably fixes an electronic element 4, which comprises a feed electrode 5. By way of example, the feed electrode 5 has a base (not shown) associated with a receiving means of the holder. Also formed on the feed electrode 5 is a signal terminal 7 which couples a signal cable 8 to the feed electrode 5. The signal cable 8 couples to a pacemaker 9, which in the arrangement 1 shown in FIG. 2 is fixed to a plastic mesh 3. In the arrangement 1 shown in FIG. 1, the pacemaker 9 is fixed to a further plastic mesh (not shown) which is fixed intracorporally. Preferably, a further holder (not shown) may be provided which is fixed to the plastic mesh 3 or to the further plastic mesh and by means of which the pacemaker 9 is releasably fixed to the plastic mesh 3 or to the further plastic mesh. However, it may also be provided that the pacemaker 9 may is fixed extracorporally or intracorporally without the carrier device 2. By way of example, the pacemaker 9 may be fixed in the region of the subcutaneous tissue. Furthermore, a thorn 10 is arranged on the carrier device 2. In an embodiment which is not shown, the thorn 10 and the feed electrode 5 are formed in an integrated manner.

During the implanting operation, the plastic mesh 3 is placed on an organ or an organ part (not shown) and is provisionally fixed there. For this, the thorn 10 is inserted into the organ. The plastic mesh 3 is preferably adhesively bonded to the organ, for example by means of a fibrin adhesive. In this case, the plastic mesh 3 is placed on the organ and then the fibrin adhesive is applied to the plastic mesh 3, preferably by spraying. A fibrin mesh thus formed encloses at least partially the plastic mesh 3 and thus fixes the plastic mesh 3 to the organ. As a result of the contact between the plastic mesh 3 and the organ, an inflammation reaction is triggered in the organ, which leads to a scar tissue or to scar formation. The scar tissue encloses at least partially the plastic mesh 3 and thus permanently fixes the plastic mesh 3 to the organ. The fibrin mesh is dissolved or lyzed by the body over time. The plastic mesh 3 is thus ultimately permanently fixed to the organ by means of bodily tissue, namely the scar tissue. It may for example also be provided that the plastic mesh 3 is stitched to the organ by means of sutures (not shown) made from a bioresorbable material.

Figure 3:
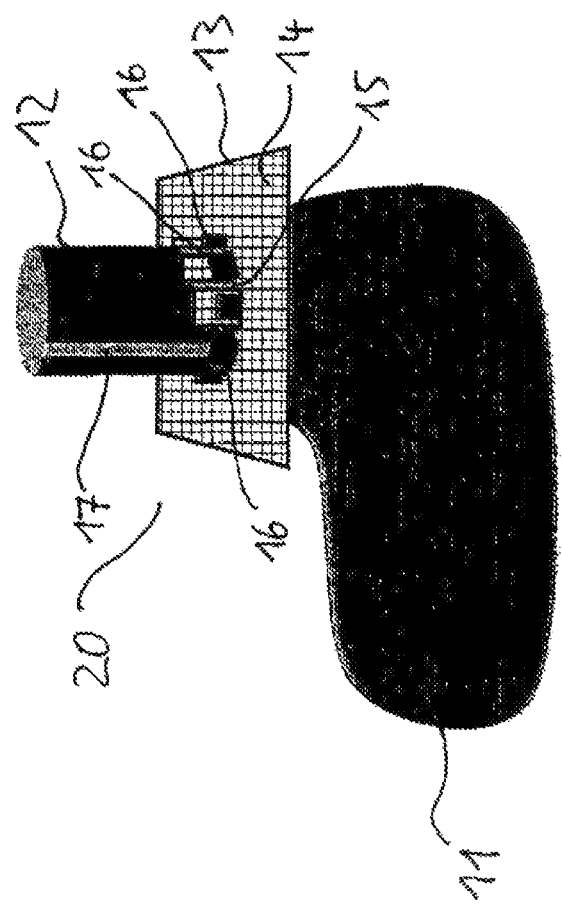
FIG. 3 shows an implanted arrangement on a stomach.
Figure 4:
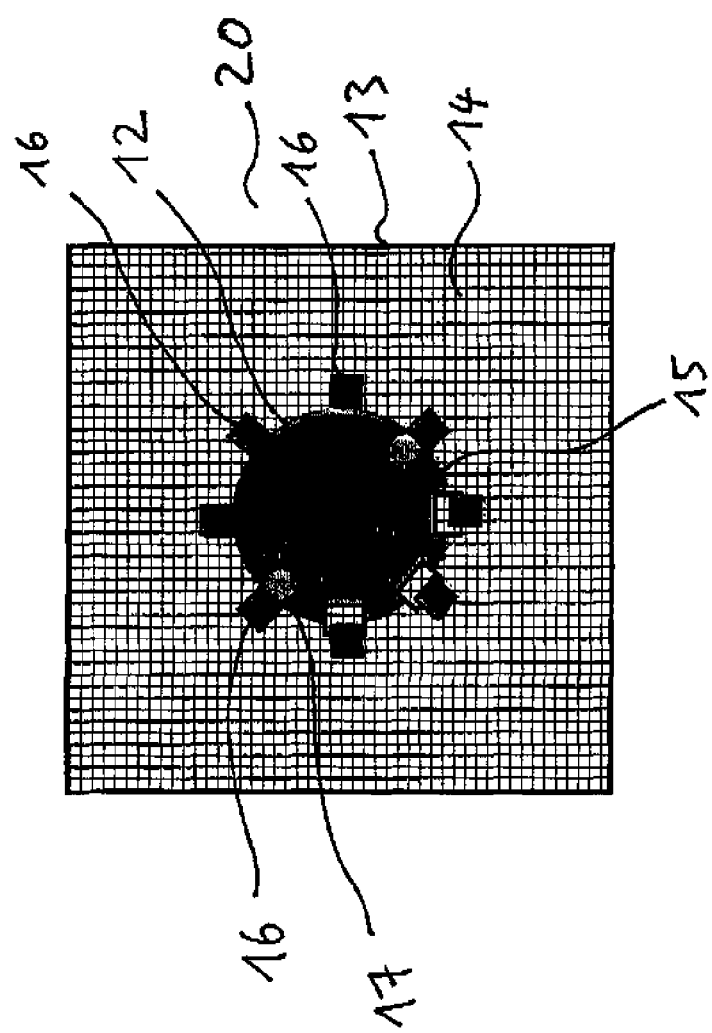
FIG. 4 shows a partial view from above of the arrangement used in FIG. 3.

FIG. 3 shows an arrangement 20 for implanting in a human or animal body, comprising a carrier device 13 which is fixed between a stomach 11 and an esophagus 12 by means of thorns (not shown). FIG. 4 shows a partial view from above of the arrangement 20 used in FIG. 3. The carrier device 13 comprises a plastic mesh 14 with an opening 15. Around the opening 15, a plurality of feed electrodes 16 are fixed to the plastic mesh 14. The transition between the stomach 11 and the esophagus 12 is arranged in the opening 15, with a diameter of the opening 15 being adapted accordingly to the transition such that the feed electrodes 16 bear against the transition tissue. The arrangement 20 thus makes it possible to stimulate the vagus nerve 17 running along the esophagus. Furthermore, the arrangement 20 may also stimulate a sphincter of the esophagus and/or of the cardia.

The features of the invention which are disclosed in the above description, the claims and the drawing may be important both individually and in any combination for implementing the invention in its various embodiments.

The invention claimed is:

1. An arrangement for implanting in a human or animal body, comprising:
   a carrier device which is made from a synthetic mesh or fabric material;
   a holder fixed to the carrier device, the holder having a receiving means; and
   an electronic element having a base, wherein the base is associated with the receiving means and is received by the receiving means of the holder such that the electronic element is replaceably and releasably fixed to the carrier device in the holder, wherein the electronic element has a thorn, wherein the electronic element and the thorn are formed in an integrated manner, and wherein the thorn is arranged on a first side of the carrier device and the electronic element is arranged on a second side of the carrier device opposing the first side, when the electronic element is fixed to the carrier device;
   wherein, when the arrangement is adapted to be implanted into the human or animal body, the carrier device is adapted to be attached to an organ or organ part, and the electronic element is replaceably fixed to the carrier device by the holder such that the electronic element is adapted to be held to the organ or organ part.

2. The arrangement according to claim 1, wherein the electronic element has a feed electrode which is configured to emit electrical pulses.

3. The arrangement according to claim 1, wherein the electronic element has a probe electrode which is configured to detect measurement signals.

4. The arrangement according to claim 1, wherein the electronic element has a pacemaker which is configured to emit pacemaker pulses.

5. The arrangement according to claim 1, wherein the electronic element has a signal terminal which is configured to couple an electrical signal link to the electronic element.

6. The arrangement according to claim 1, wherein the electronic element has a supply terminal which is configured to receive an electrical power supply for the electronic element.

7. The arrangement according to claim 1, wherein the electronic element has a data terminal which is configured to couple an electronic data link to the electronic element.

8. The arrangement according to claim 1, wherein the synthetic mesh or fabric material is formed according to at least one material configuration selected from the following group of material configurations: plastic mesh, plastic-coated mesh, synthetic fibers, material of plant origin, metal material, organic material, inorganic material, at least partially resorbable material and electrically conductive material.

9. The arrangement according to claim 1, wherein an opening is formed in the region of the receiving means.

10. The arrangement according to claim 9, wherein the electronic element is arranged adjacent to the opening.

11. The arrangement according to claim 1, wherein the carrier device and the electronic element fixed to the carrier device are configured to be implanted on or in an organ or an organ part selected from the following group of organs/organ parts: esophagus, stomach, reflux muscle, heart, bladder, sphincter, cardia, fundus, corpus, vagus nerve, brain, muscles, nerves, pelvic floor and rectum.

12. The arrangement according to claim 1, wherein the electronic element is releasable when the arrangement is implanted in the human or animal body and when the carrier device is adapted to be attached to an organ or organ part.

13. The arrangement according to claim 1, wherein the electronic element is releasable when the arrangement is fully assembled.

14. A method for implanting an arrangement in a human or animal body, comprising:
providing an arrangement comprising a carrier device that is made from a synthetic mesh or fabric material, a holder fixed to the carrier device, the holder having a receiving means, and an electronic element having a base wherein the base is associated with the receiving means and is received by the receiving means of the holder such that the electronic element is replaceably and releasably fixed to the carrier device in the holder, wherein the electronic element has a thorn, wherein the electronic element and the thorn are formed in an integrated manner, and wherein the thorn is arranged on a first side of the carrier device and the electronic element is arranged on a second side of the carrier device opposing the first side, when the electronic element is fixed to the carrier device; and
implanting the arrangement by attaching the carrier device to a tissue section in an interior of the body and provisionally fixing it thereto;
wherein, when the carrier device is attached to the tissue section, the electronic element is replaceably fixed to the carrier device by the holder such that the electronic element is held to the tissue section.

15. The method according to claim 14, wherein the step of provisional fixing comprises a step of adhesively bonding the carrier device to the tissue section.

16. The method according to claim 14, wherein the step of provisional fixing comprises a step of mechanically attaching the carrier device to the tissue section using mechanical fixing means.

17. The method according to claim 14, wherein a step is also provided for permanently fixing the carrier device to the tissue section as a result of the fact that scar formation takes place on the tissue section around the carrier device.

18. The method according claim 14, wherein a step is also provided for feeding stimulation pulses to the tissue section via the electronic element having a feed electrode.

19. The method according to claim 18, wherein a step is also provided for emitting pacemaker pulses to the feed electrode and/or to the probe electrode via the electronic element having a pacemaker.

20. The method according to claim 14, wherein a step is also provided for detecting measurement signals for the tissue section via the electronic element having a probe electrode.

21. The method according to claim 14, wherein an electrical signal link is coupled to the electronic element.

22. The method according to claim 14, wherein the electronic element is supplied with electrical power.

23. The method according to claim 14, wherein an electronic data link is coupled to the electronic element.

24. The method according to claim 14, wherein the arrangement is introduced into the human or animal body by means of a laparoscopic operating method.

25. The method according to claim 14, wherein the arrangement is implanted on the tissue section of an organ or an organ part selected from the following group of organs/organ parts: esophagus, stomach, reflux muscle, heart, bladder, sphincter, cardia, fundus, corpus, vagus nerve, brain, muscles, nerves, pelvic floor and rectum.

26. The method according to claim 14, wherein the electronic element is releasable when the arrangement is implanted in the human or animal body and when the carrier device is attached to the tissue section.

27. The method according to claim 14, wherein the electronic element is releasable when the arrangement is fully assembled.

* * * * *